(12) United States Patent
Seybold et al.

(10) Patent No.: US 10,702,159 B2
(45) Date of Patent: Jul. 7, 2020

(54) SYSTEM AND APPARATUS FOR CAPTURING AND NAVIGATING WHOLE BODY IMAGES THAT INCLUDES HIGH RESOLUTION BODY PART IMAGES

(71) Applicant: DermSpectra LLC, Tucson, AZ (US)

(72) Inventors: Karleen Seybold, Tucson, AZ (US); Eugene Balaguer, Austin, TX (US); Nathaniel Santana, Sterling, VA (US)

(73) Assignee: Techara LLC, Concord, NH (US)

( * ) Notice: Subject to any disclaimer, the term of this patent is extended or adjusted under 35 U.S.C. 154(b) by 338 days.

(21) Appl. No.: 15/076,535

(22) Filed: Mar. 21, 2016

(65) Prior Publication Data

US 2016/0270664 A1  Sep. 22, 2016

Related U.S. Application Data

(60) Provisional application No. 62/136,298, filed on Mar. 20, 2015.

(51) Int. Cl.
| | |
|---|---|
| *H04N 7/18* | (2006.01) |
| *A61B 5/00* | (2006.01) |
| *H04N 5/232* | (2006.01) |
| *H04N 5/247* | (2006.01) |

(52) U.S. Cl.
CPC .......... *A61B 5/0077* (2013.01); *A61B 5/6888* (2013.01); *H04N 5/23238* (2013.01); *H04N 5/23293* (2013.01); *H04N 5/247* (2013.01); *A61B 5/70* (2013.01)

(58) Field of Classification Search
CPC .................................................. A61B 5/0077

USPC .......................................................... 348/77
See application file for complete search history.

(56) References Cited

U.S. PATENT DOCUMENTS

| | | | |
|---|---|---|---|
| 5,117,283 A | 5/1992 | Kroos et al. | |
| 8,351,770 B2 | 1/2013 | DePaula et al. | |
| 2001/0028730 A1* | 10/2001 | Nahata | G06K 9/00597 382/117 |
| 2005/0117049 A1* | 6/2005 | Suzuki | H04N 5/23212 348/345 |
| 2006/0251408 A1* | 11/2006 | Konno | A61B 5/4547 396/14 |
| 2009/0118600 A1* | 5/2009 | Ortiz | A61B 5/0064 600/306 |
| 2009/0185727 A1* | 7/2009 | Beckmann | A61B 5/1171 382/128 |
| 2010/0134695 A1* | 6/2010 | O'Connell | A63J 5/021 348/722 |
| 2013/0296711 A1 | 11/2013 | Curiel et al. | |
| 2014/0012831 A1 | 1/2014 | Wallen et al. | |
| 2014/0243684 A1 | 8/2014 | Curiel et al. | |
| 2014/0267425 A1* | 9/2014 | Moll | G06T 13/80 345/638 |
| 2014/0289312 A1* | 9/2014 | Jafarifesharaki | H04L 67/42 709/203 |

* cited by examiner

*Primary Examiner* — Leron Beck
(74) *Attorney, Agent, or Firm* — Zeman-Mullen & Ford, LLP (57) ABSTRACT

A system and method for capturing and navigating whole body images that includes capturing a total body image with a wide angle lens camera and simultaneously capturing body part images of the same body using a plurality of high resolution cameras. The total body image is used as a navigational grid that is associated with the high resolution body part images.

15 Claims, 13 Drawing Sheets

SYSTEM AND APPARATUS FOR CAPTURING AND NAVIGATING WHOLE BODY IMAGES THAT INCLUDES HIGH RESOLUTION BODY PART IMAGES

CROSS-REFERENCE TO RELATED APPLICATIONS

This application claims priority to provisional patent application having Ser. No. 62/136,298, filed Mar. 20, 2015, which is herein incorporated by reference in its entirety, and is related to patent application having Ser. No. 13/778,942, filed Feb. 27, 2013, patent application having Ser. No. 13/781,735, filed Feb. 28, 2013, and patent application having Ser. No. 14/860,509, filed Sep. 21, 2015, all of which are also herein incorporated by reference in their entireties.

FIELD OF INVENTION

The present invention is directed to a system and apparatus for capturing and navigating whole body images that is especially useful for capturing and navigating skin images. The system and apparatus uses a camera with a wide angle camera lens to capture a whole body image and a plurality of high resolution body part cameras that are used to capture body part images. By utilizing software to trigger the cameras, all images are taken simultaneously so that the camera with the wide angle lens and the multiple high resolution cameras are used to take images at the same time. One exemplary embodiment of the invention utilizes one wide angle lens camera and eight high resolution cameras to capture nine images at the same time. However, it will be understood by those skilled in the art that any multiple number of high resolution cameras may be used to take images of the body parts as long as the images of the body parts add up to total a full body image. The present invention assists in providing an automated, standardized, and reproducible process for image acquisition, post-processing of images, and archiving and display of images, all used especially for automated total body skin imaging.

BACKGROUND OF THE INVENTION

Although several methods and apparatus exist in the prior art for imaging and recording a patient's skin, the present invention was created to efficiently, effectively, and easily display skin images and identify and record observations relating to those skin images including skin abnormalities and areas of concern. The present invention was also created to easily make side by side image comparisons of the same areas of the skin taken at different times and to enable sharing of those displayed images, compared images, and recorded observations relating to those images with patients, health care workers, and health care related entities.

SUMMARY OF THE INVENTION

The present invention is directed to a system and apparatus for capturing and navigating whole body images that is especially useful for capturing and navigating skin images. One exemplary embodiment of the total body imaging apparatus of the present invention includes an enclosed interior area, a camera with a wide angle lens located within the enclosed interior area and positioned to capture the total body image of a user, and a plurality of high resolution cameras located within the enclosed interior area and positioned to capture different body portions or body parts of the user. The enclosed interior area may include a front panel having a plurality of openings where the front panel is placed in front of the cameras so that a lens of the wide angle lens camera and a lens of each of the plurality of high resolution cameras cane be seen through the respective openings in the front panel. The high resolution cameras capture different portions or parts of the user's body such that taken together they form a total body image of the user. The wide angle lens camera may be positioned between two rows of cameras that make up the plurality of high resolution cameras.

In another exemplary embodiment of the invention, the total body imaging apparatus includes a single wide angle lens camera and eight high resolution cameras. The eight high resolution cameras may be configured to form a first row of three cameras, a second row of three cameras located below the first row of three cameras, and a third row of two cameras located below the second row of three cameras. The wide angle lens camera may be positioned between the first row of three high resolution cameras and the second row of three high resolution cameras.

The total body imaging apparatus of the present invention may also include a computer processing unit in communication with one or more program applications related to the use of the total body imaging apparatus. One such program application may trigger the wide angle lens camera and the plurality of high resolution cameras to simultaneously capture images and to arrange the eight high resolution body part images taken with the eight high resolution cameras for a particular body pose and associate them with the total body image captured with the wide angle lens camera for the same body pose. The program application may further use the total body image taken with the wide angle lens camera as a navigational grid by sectioning or dividing the total body image into sections or tiles that correspond to the location of the eight high resolution cameras and their related high resolution body part images where any of the eight sections or tiles can be selected and magnified to further view in more detail an area of skin contained within the selected section or tile.

The program application may further include a reduced size image of the eight section/tile navigational grid displayed on a magnified image of a selected section/tile of the navigational grid that has been selected for viewing in more detail. The reduced size image of the eight section/tile navigational grid may be displayed in the lower right side of the magnified selected section/tile image of the navigational grid. The program application may further include the ability to further magnify and annotate the high resolution body part image (from one of the eight high resolution cameras) that is associated with the selected section/tile of the total body image taken with the wide angle camera lens.

In still another exemplary embodiment, the total body imaging system of the present invention includes a wide angle lens camera positioned to capture a total body image of a user, a plurality of high resolution cameras positioned to capture different body portions of the user's total body where the wide angle lens camera and the plurality of high resolution cameras capture images simultaneously, and a computer processing unit in communication with at least one program application that arranges high resolution body part images taken with the plurality of high resolution cameras for a particular pose and associates them with the total body image of the user captured with the wide angle lens camera. The program application may use the total body image taken with the wide angle lens camera as a navigational grid by sectioning the total body image into sections that correspond to the location of the plurality of high resolution cameras and their related high resolution body part images where any of the sections can be selected and magnified to further view in more detail an area of skin contained within the selected section.

The program application may further include a reduced size image of the sectioned navigational grid displayed on a magnified image of a selected section of the navigational grid that has been selected for viewing in more detail. The program application may also include the ability to further magnify and also annotate the high resolution body part image that is associated with the selected section of the total body image navigational grid.

In addition, the program application of the present invention may also include the abilities and features described in the program application discussed and exemplified in Applicant's related patent application having Ser. No. 14/860,509. These additional abilities and features include the ability to draw one or more different boundary configurations around areas of concern identified in the images, the ability to descriptively identify the location on the body of the areas of concern as well as the ability to notate comments and observations about the areas of concern, the ability to record a diagnosis and/or medical code relating to the areas of concern, the ability to compare the area or areas of concern with previous recorded images of the same area or areas of concern to enable a side by side comparison of the area or areas of concern taken at different times, and the ability to share images of concern with the user/patient, other healthcare professionals, and/or health care related entities via a wired and/or wireless connection.

BRIEF DESCRIPTION OF THE DRAWINGS

The subject invention will hereinafter be described in conjunction with the appended drawing figures which depict portions of the total body imaging apparatus as well as exemplary screen shots of a graphical user interface (GUI) seen by a physician/healthcare worker while viewing skin care images of a user/patient in accordance with the total body imaging system of the present invention, and where.

DETAILED DESCRIPTION OF EXEMPLARY EMBODIMENTS

The system and apparatus for capturing and navigating whole body images that includes high resolution body part images is generally directed to exemplary embodiments which include a camera with a wide angle lens positioned to capture the total body image of a user, a plurality of high resolution cameras positioned to capture different body portions or body parts of the user's total body where the wide angle lens camera and the plurality of high resolution cameras capture images simultaneously; and a computer processing unit in communication with at least one program application that arranges high resolution body part images taken with the plurality of high resolution cameras for a particular pose and associates them with the total body image of the user captured with the wide angle lens camera for the same pose. The program application also uses the total body image of the user as a navigational grid by sectioning the total body image into sections that correspond to the location of the plurality of high resolution cameras and their related high resolution body part images where any of the sections can be selected and magnified to further view in more detail an area or areas of skin contained within the high resolution body part image associated with the selected section. Although there are many devices capable of capturing a plurality of images of a person/patient, some exemplary embodiments of such a device can be found in patent application having Ser. No. 13/778,942 which is herein incorporated by reference in its entirety. Further, although there are many examples of servers and processors capable of being in communication with program applications, some exemplary embodiments of such elements can be found in patent application having Ser. No. 13/781,735 which is herein incorporated by reference in its entirety. In addition, although there are many examples of recording, magnifying, and annotating photographic images, some exemplary embodiments can be found in patent application having Ser. No. 14/860,509 which is herein incorporated by reference in its entirety. It will be understood by those skilled in the art that although exemplary embodiments of some of the functional elements included in the present invention can be found in these cited pending applications, many other similar elements may be used in the present invention to assist in providing the unique viewing and recording features that make the system and method of the present invention novel. It should also be noted that the total body image of the user that is used to create the human body navigational grid of the present invention is obtained from the wide angle lens camera of the present invention and that each section or tile of the navigational grid, when selected for further in depth viewing, is associated with high resolution body part images of the user that are obtained from the plurality of high resolution cameras of the present invention.

Figure 1:
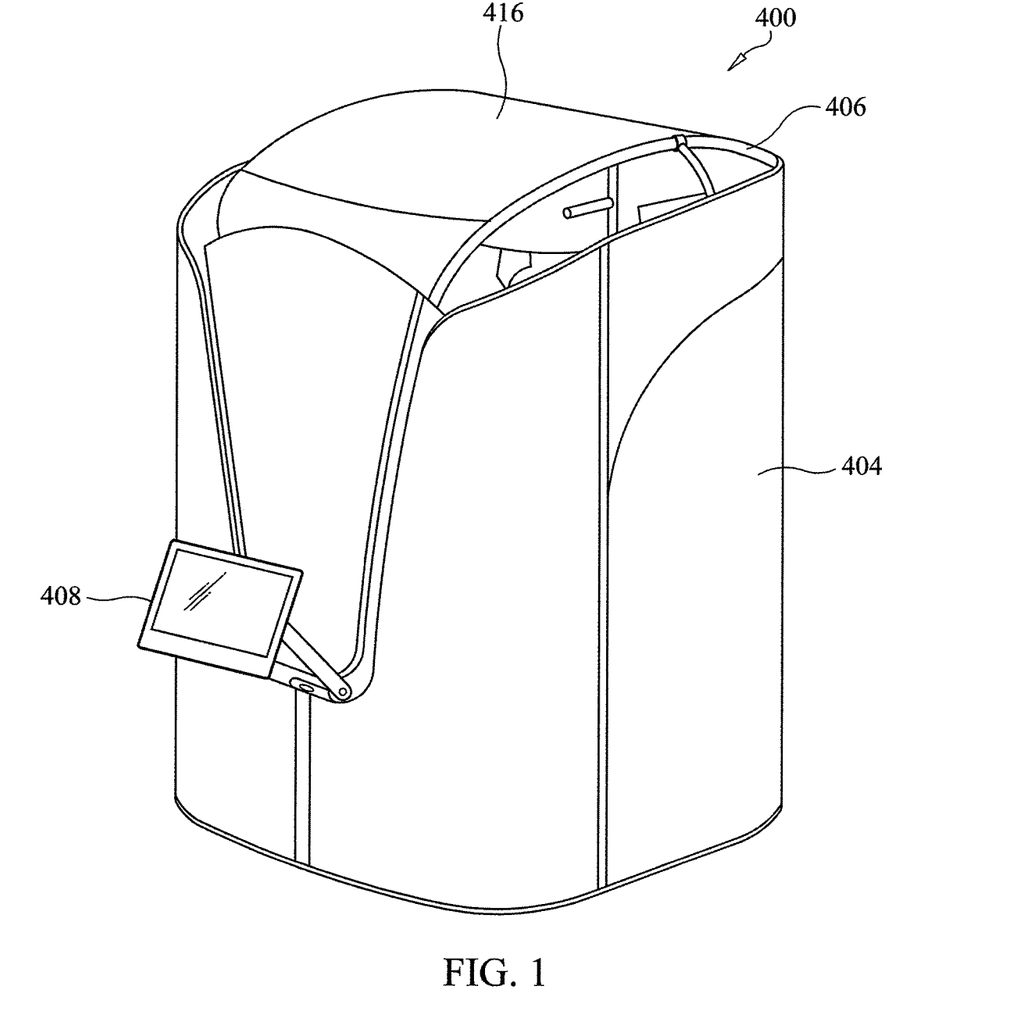
FIG. 1 is an outer perspective view of an exemplary embodiment of the total body imaging apparatus in accordance with the present invention.
Figure 2:
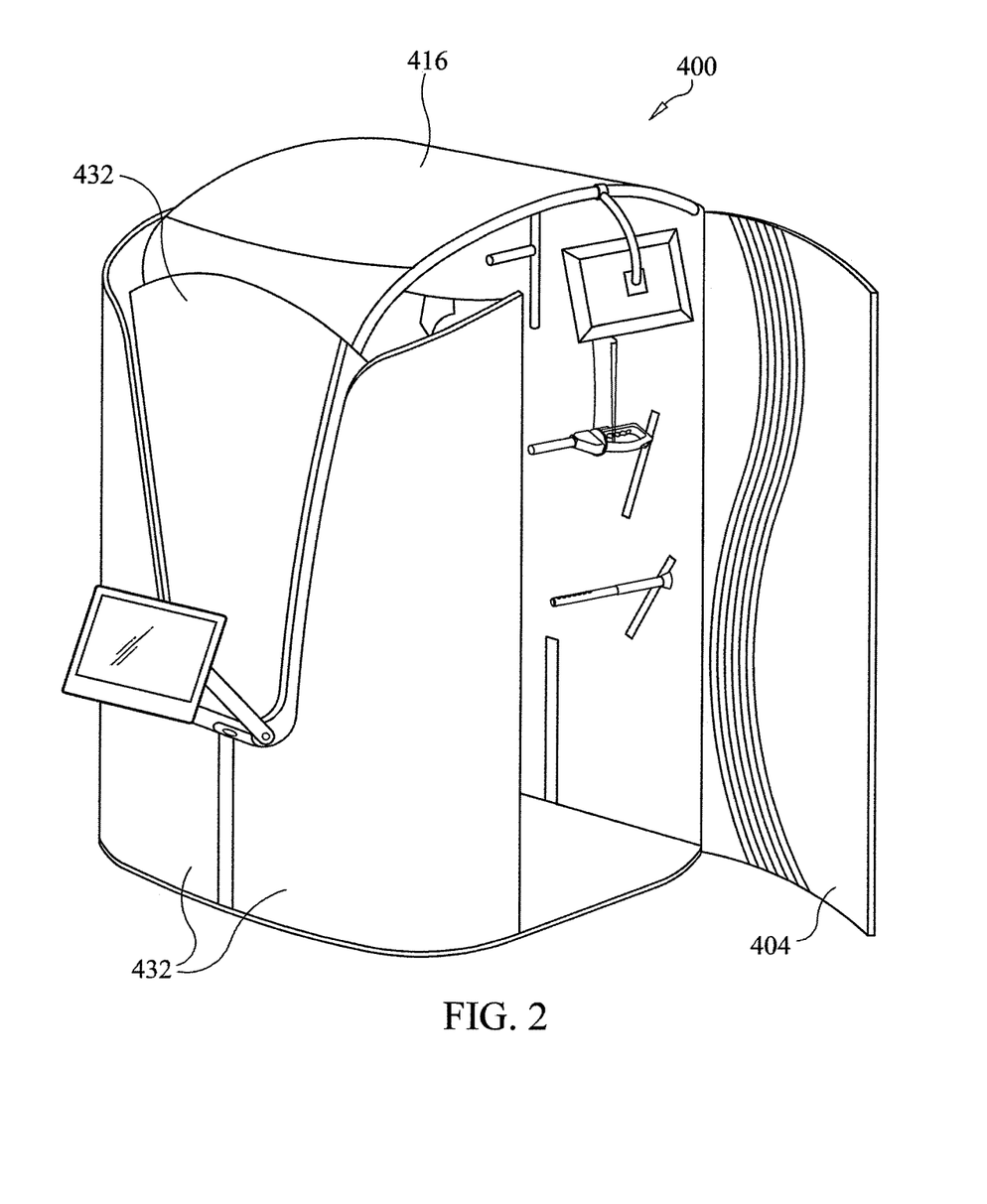
FIG. 2 is an outer perspective view of the exemplary embodiment of the total body imaging apparatus of the present invention depicted in FIG. 1 with a door of the total body imaging apparatus shown open.

FIG. 1 shows an outer perspective view of an exemplary embodiment of the total body imaging apparatus 400 in accordance with the present invention. Total body imaging apparatus 400 includes an enclosed interior area 402, a door 404 enabling a user of the imaging apparatus to enter the enclosed interior area, and a plurality of cameras (see FIG. 4) which together provide a total body image taken with a wide angle lens camera and a plurality of different high resolution body part images taken with a plurality of high resolution cameras where all of the images are taken simultaneously for any given predetermined body pose. The cameras exist in stationary positions and are not capable of repositioning. The imaging station/booth 400 also includes a technician computer device 408 that may be adjustably connected to an outer surface of the imaging apparatus 400 to enable a technician to control the program applications associated with the use of the imaging apparatus 400. The imaging apparatus 400 has a curved roof to create an open feeling for those users having their images taken within the enclosed interior area 402. It should be noted that the enclosed interior area 402 may be an area that is fully enclosed or an area that is mostly fully enclosed as exhibited in the imaging apparatus 400 shown in FIG. 1. FIG. 2 is an outer perspective view of the exemplary embodiment of the imaging apparatus 400 of the present invention depicted in FIG. 1 with the door 404 of the imaging apparatus 400 shown open.

Figure 3:
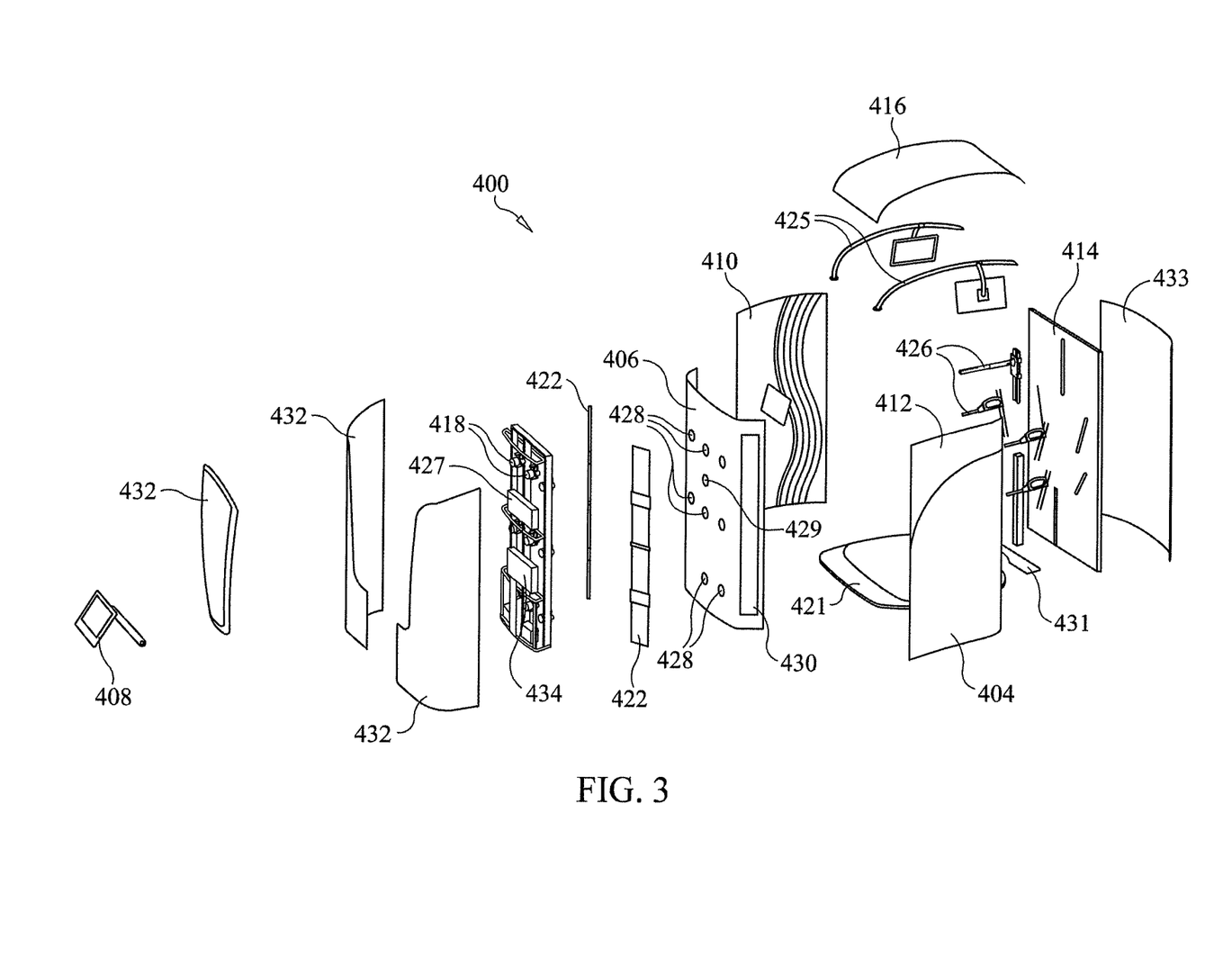
FIG. 3 is an exploded view of the exemplary embodiment of the total body imaging apparatus of the present invention shown in FIG. 1.

FIG. 3 is an exploded view of the exemplary embodiment of the imaging apparatus 400 of the present invention shown in FIG. 1. As shown in FIG. 1, imaging apparatus 400 includes a front panel 406, two opposing side panels 410, 412 a rear panel 414, and a top cover member 416. The door 404 may be located within side panel 412 or entire side panel 412 may function as door 404.

Furthermore, although not shown, both side panels 410, 412 may function as doors or include doors. Imaging apparatus 400 also includes a plurality of cameras 418 that are secured to a frame 420, a floor member 421, one or more light panels 422, one or more visual display devices 424, one or more body positioning members 426, 429, and at least one speaker component 427. The speaker component 427 enables a user to hear voice instructions within the enclosed interior area 402 and the visual display device(s) 424 are located within the enclosed interior area 402 such that they are viewable by a user. This enables a user to receive audio and visual instructions for undertaking a series of one or more predetermined body poses so that the cameras 418 can capture images of the user in the various body poses.

Front panel 406 includes a plurality of circular openings 428 for the lenses of the cameras 418 to be positioned within, or seen therethrough, in order to provide camera access to the enclosed interior area 402 of the imaging apparatus 400, and at least two vertically oriented rectangular openings 430 that enable each of the light panels 422 to be inserted therethrough so that light is provided to the enclosed interior area 402 of the imaging apparatus 400 so that cameras 418 can capture readable images of users in one or more series of predetermined poses. The light panels 422 are positioned on opposing sides of the cameras 418 so that the enclosed interior area 402 will be properly lit for taking images of users. Further details of the cameras 418 and the front panel 406 with openings 428 are discussed with reference to FIGS. 4-6.

The body positioning members 426, 429 located within the enclosed interior area 402 enable a user to accurately position his/her body in a series of one or more predetermined body poses. The body positioning members 426, 429 include one or more handles 426 for a user's hands and a footplate 429 for the user's foot or feet. One or more outlined areas for placement of the user's feet may also be included on the floor member 421 and/or footplate 429 of the imaging apparatus 400. The handles 426 and/or footplate 429 may further include a light emitting component with capacitive touch sensors which enable the handles 426 and/or footplate 429 to light up when properly engaged by a user in order to accurately pose in a series of one or more predetermined body poses. The handles 426 may be secured to the rear panel 414 of the imaging apparatus 400 and the footplate 429 may be movable and retractable within floor member 421 of the imaging apparatus 400. Visual display device(s) 424 may be attached to and supported by bar members 425 which are connected to the imaging apparatus 400. Imaging apparatus 400 may also include one or more moveable or removable outer front panels 432 which can be moved to access the cameras 418, an outer rear panel 433, a frame 420, one or more speaker component(s) 427 and other components such as a computer processing unit 434 that is in communication with one or more program application(s) related to the use of the imaging apparatus 400.

Program application(s) may include one or more of i) a program application for taking, capturing, and storing the images produced by cameras 418, ii) an automatic focusing algorithm to automate focusing of cameras 418 by determining an area of interest for each camera 418 in each of the one or more predetermined poses undertaken by a user, iii) a program application that arranges high resolution body part images of a user taken with a plurality of high resolution cameras, associates them with a total body image of the user captured with a wide angle lens camera, and creates a navigational grid using the total body user image that enables selection of the high resolution body part images; iv)

a program application that enables a medical professional and/or medical facility (such as hospitals, medical clinics, etc.) to obtain wireless access to the images in order to view the images, compare a plurality of the images of a same user taken at different times, document notes relating to the images, create electronic medical records that include the images, and/or send the images and related notes to another medical professional and/or medical facility, and v) a program application that enables a medical professional and/or medical facility having access to the images of a user to interface with other existing electronic medical record databases from other medical professionals and/or medical facilities utilized by the user so that the images of the user can be compared to other existing electronic record databases.

Figure 4:
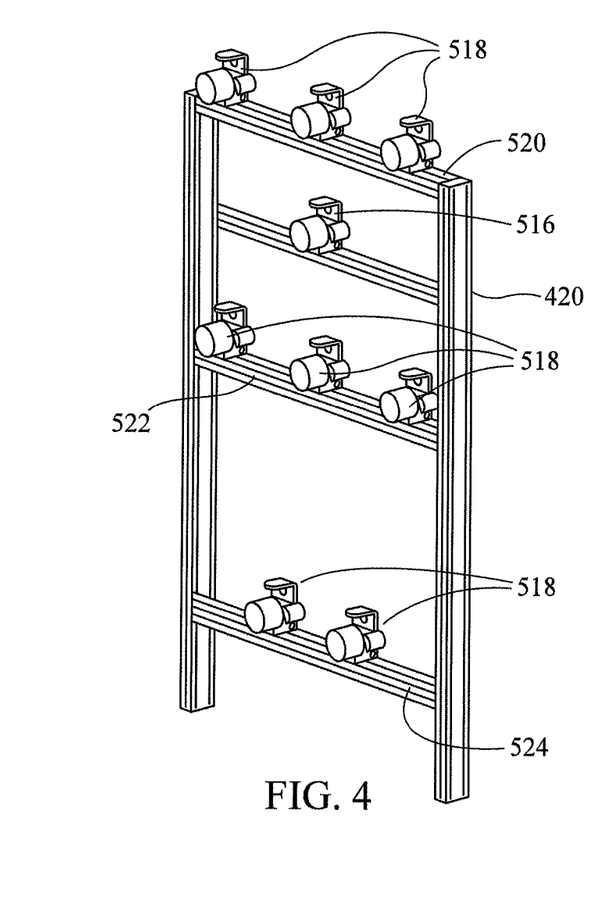
FIG. 4 is a perspective view of the plurality of cameras and the frame which supports the plurality of cameras contained in the total body imaging apparatus shown in FIGS. 1-3.

A perspective view of an exemplary embodiment of the plurality of cameras 418 and the frame 420 which supports the plurality of cameras 418 contained in the imaging apparatus 400 is shown in FIG. 4. In this exemplary embodiment, there are nine cameras each secured to frame 420. One camera is a wide angle lens camera 516 that is capable of taking a whole or total body image of a user that is positioned within the apparatus 400. Eight of the cameras are high resolution cameras 518 that are positioned to create a first row 520 of three cameras, a second row 522 of three cameras, and a third row 524 of two cameras where each row 520, 522, 524 of the high resolution cameras 518 may be equidistantly positioned from one another. Wide angle lens camera 516 is positioned between the first row 520 of three high resolution cameras 518 and the second row 522 of three high resolution cameras 518 and is attached to the frame 420 such that is located in vertical alignment with the middle high resolution camera 518 contained in first row 520 and the middle high resolution camera 518 contained in second row 522. The two high resolution cameras 518 contained in row 524 are spaced equidistant from one another but are not in vertical alignment with the high resolution cameras 518 contained in rows 520 and 522. Each of the cameras 516, 518 may be secured to the frame 420 by way of quick release level mounts.

Figure 5:
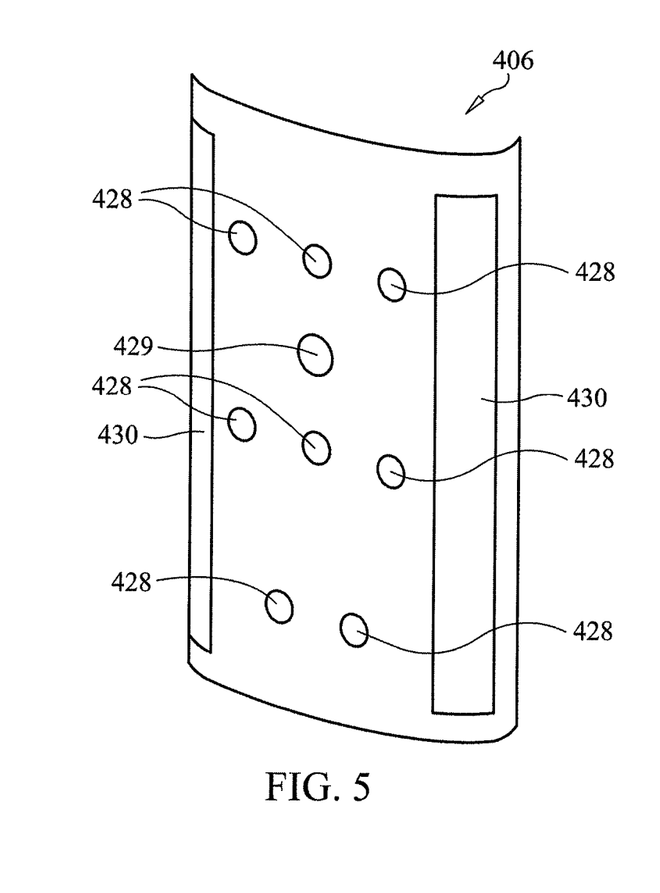
FIG. 5 is a front perspective view of the front panel of the total body imaging apparatus shown in FIGS. 1-3 having openings contained therein for the camera lenses and the light panels.
Figure 6:
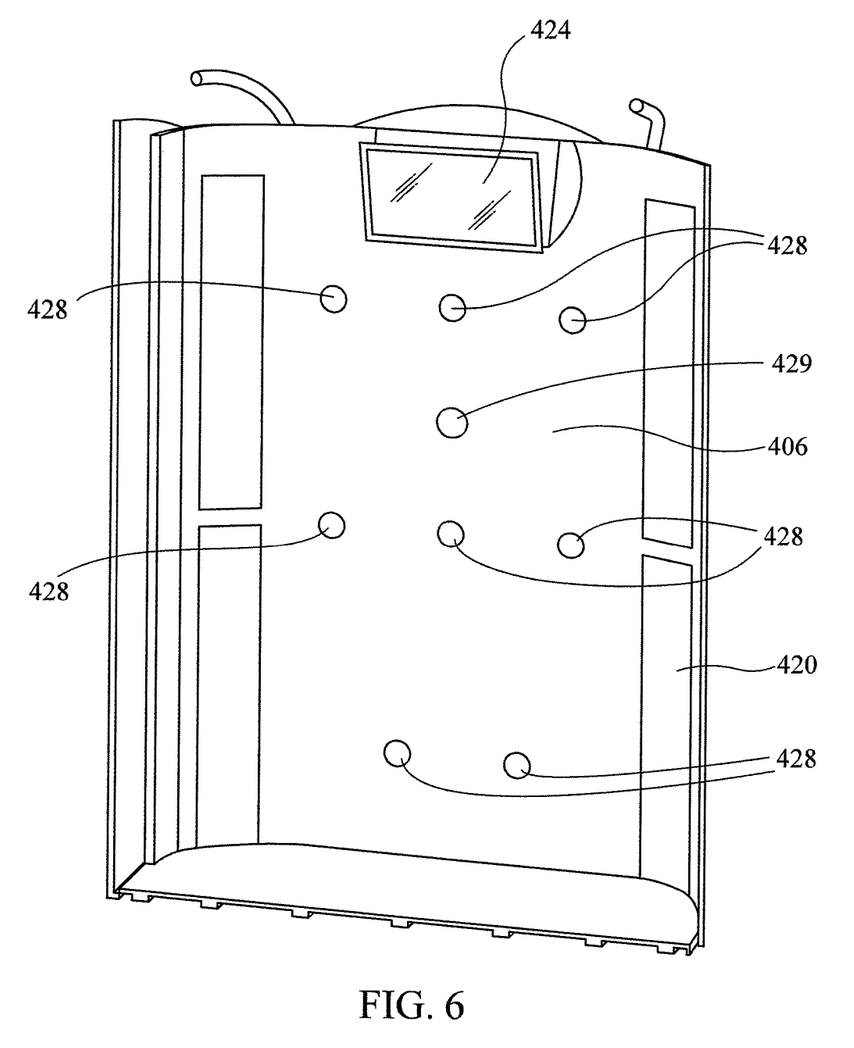
FIG. 6 a rear perspective view of the front panel of the total body imaging apparatus shown in FIGS. 1-3 and 5 showing the front panel as it looks from standing inside the total body imaging apparatus of the present invention.
Figure 7:
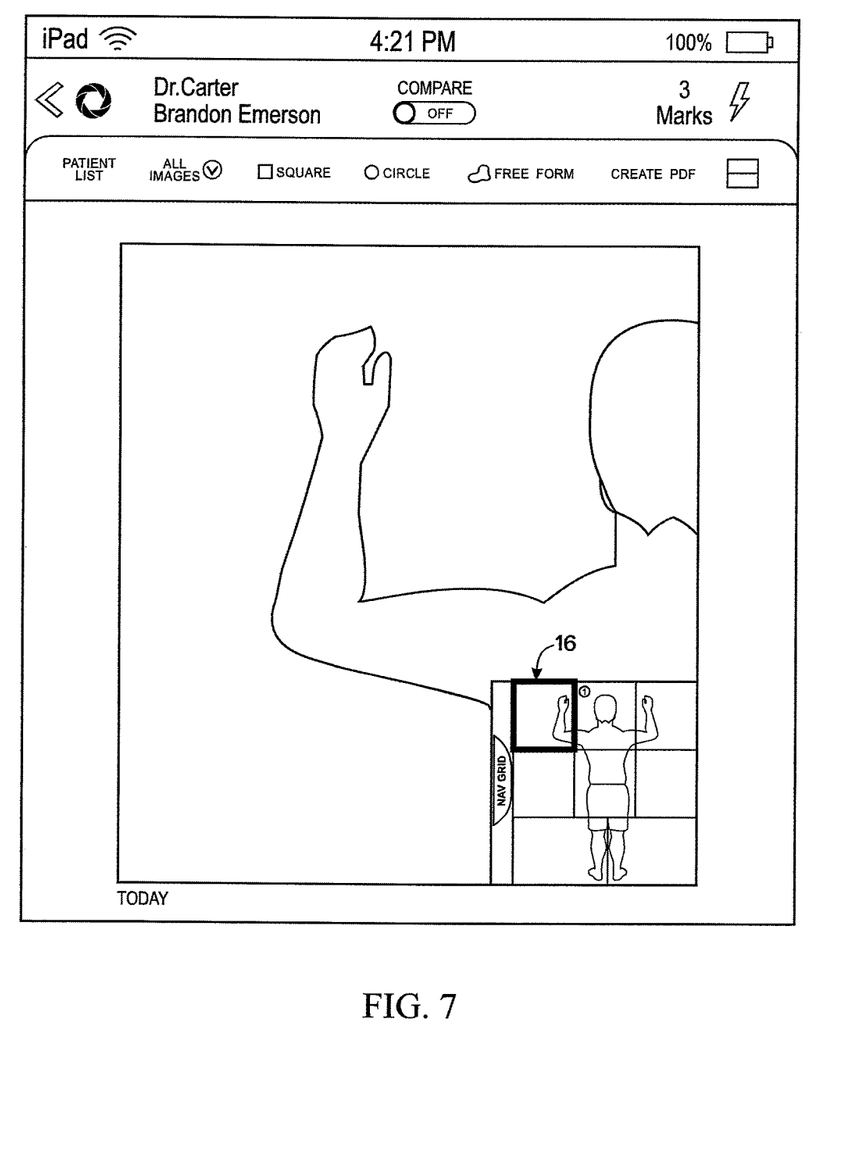
FIG. 7 is a graphical user interface (GUI) screen shot showing a reduced size image of a total body navigational grid of a user/patient that corresponds to eight high resolution camera images with the upper left tile/section of the navigational grid shown selected and the associated high resolution camera image shown magnified for more in depth viewing.
Figure 8:
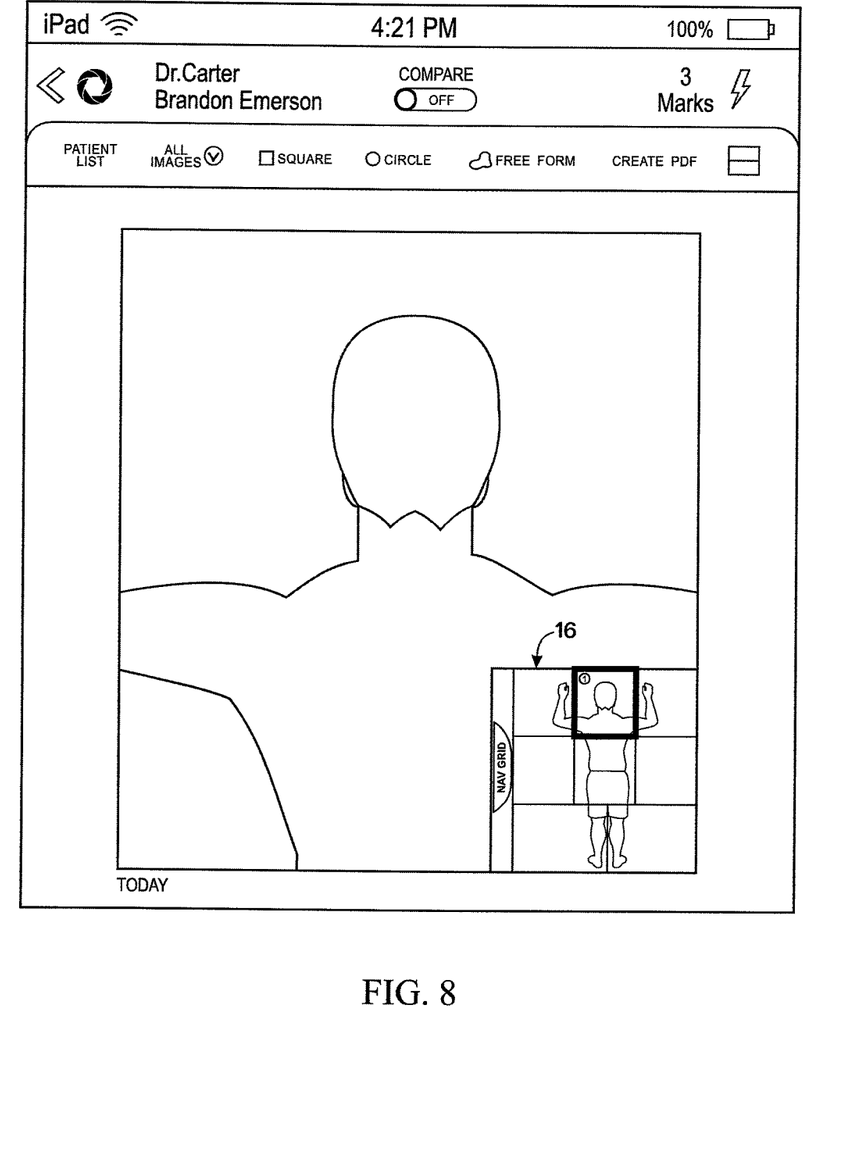
FIG. 8 is a GUI screen shot showing a reduced size image of a total body navigational grid of a user/patient that corresponds to eight high resolution camera images with the upper middle tile/section of the navigational grid shown selected and the associated high resolution camera image shown magnified for more in depth viewing.
Figure 9:
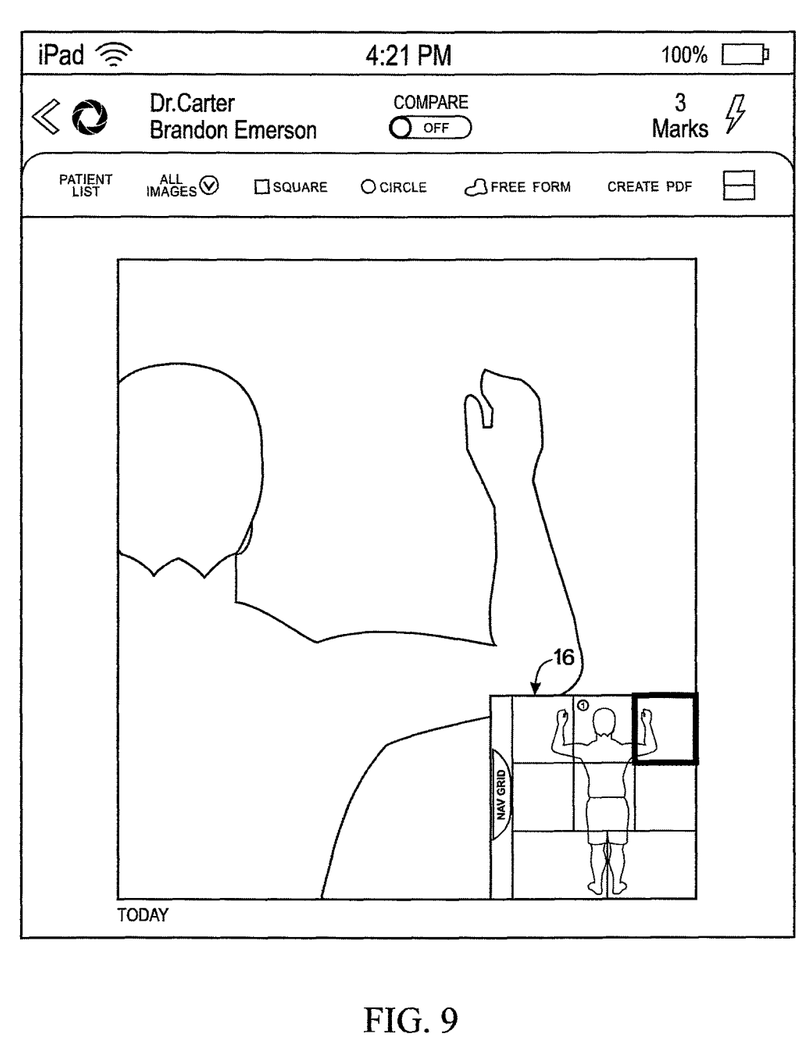
FIG. 9 is a GUI screen shot showing a reduced size image of a total body navigational grid of a user/patient that corresponds to eight high resolution camera images with the upper right tile/section of the navigational grid shown selected and the associated high resolution camera image shown magnified for more in depth viewing.
Figure 10:
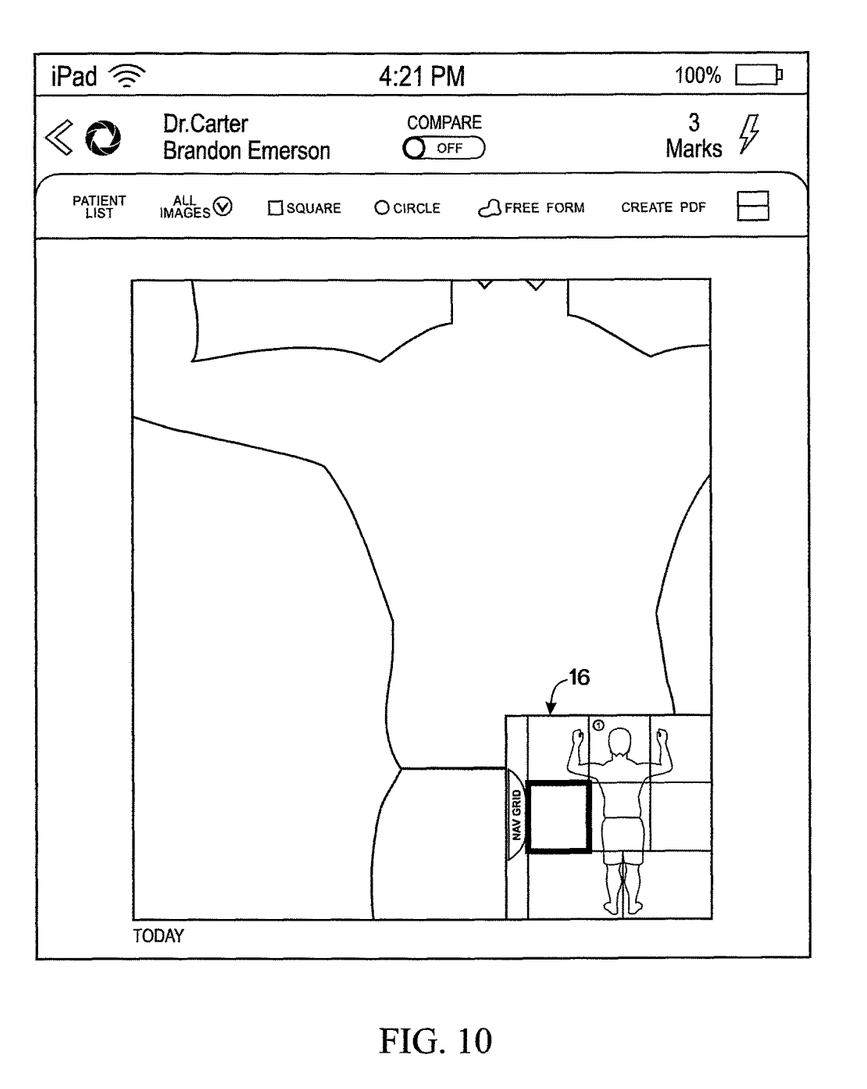
FIG. 10 is a GUI screen shot showing a reduced size image of a total body navigational grid of a user/patient that corresponds to eight high resolution camera images with the middle left tile/section of the navigational grid shown selected and the associated high resolution camera image shown magnified for more in depth viewing.
Figure 11:
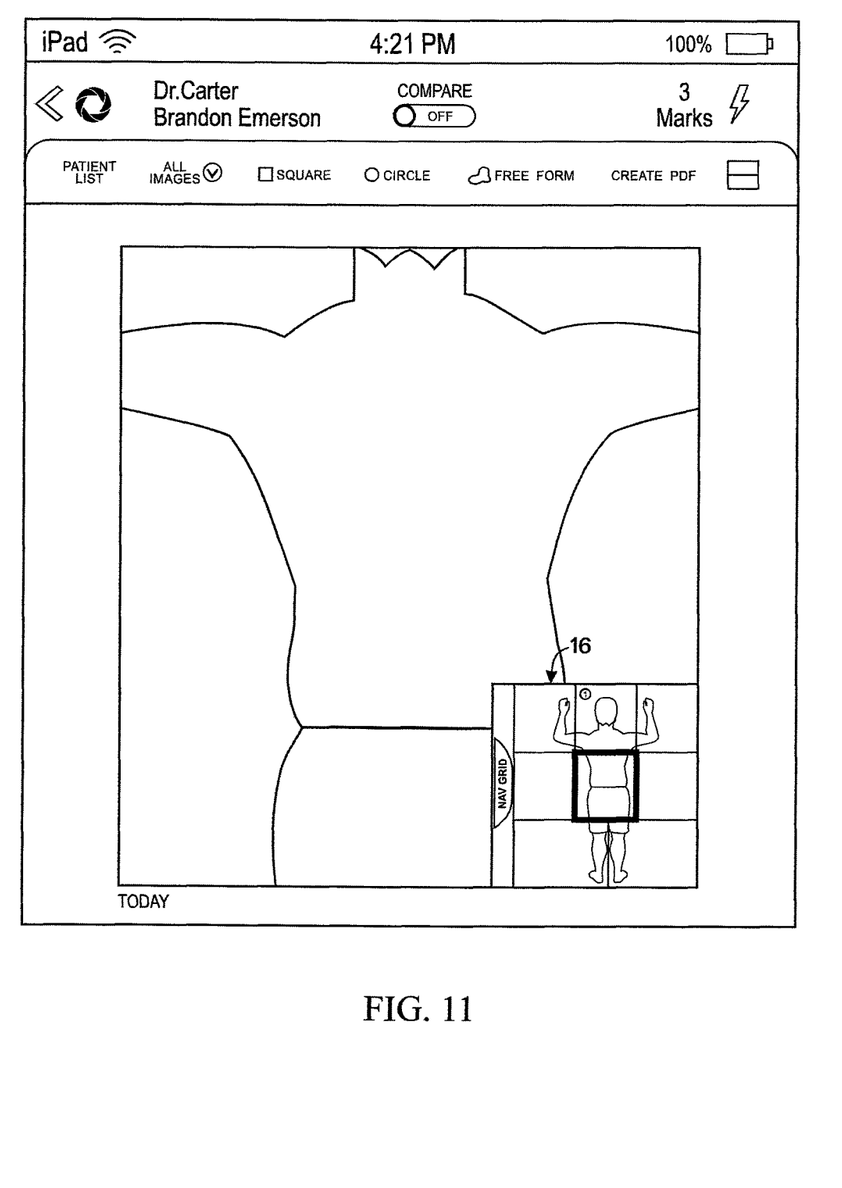
FIG. 11 is a GUI screen shot showing a reduced size image of a total body navigational grid of a user/patient that corresponds to eight high resolution camera images with the middle mid tile/section of the navigational grid shown selected and the associated high resolution camera image shown magnified for more in depth viewing.
Figure 12:
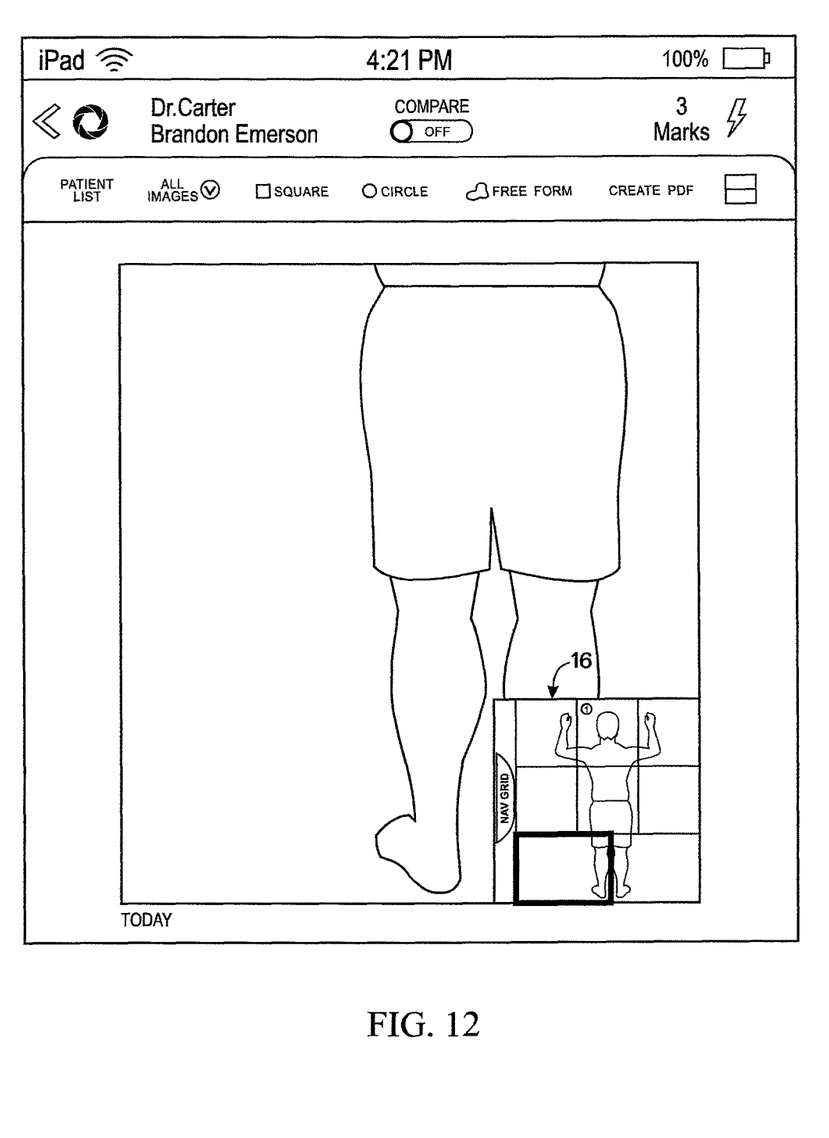
FIG. 12 is a GUI screen shot showing a reduced size image of a total body navigational grid of a user/patient that corresponds to eight high resolution camera images with the bottom left tile/section of the navigational grid shown selected and the associated high resolution camera image shown magnified for more in depth viewing.
Figure 13:
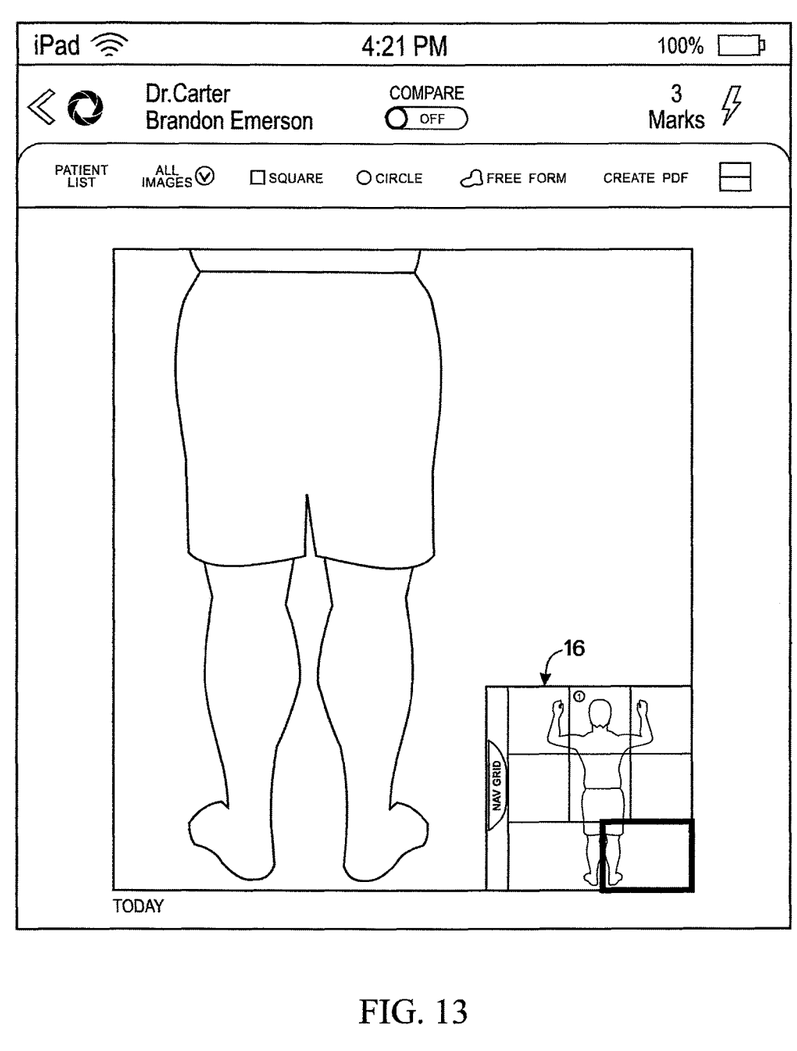
FIG. 13 is a GUI screen shot showing a reduced size image of a total body navigational grid of a user/patient that corresponds to eight high resolution camera images with the bottom right tile/section of the navigational grid shown selected and the associated high resolution camera image shown magnified for more in depth viewing.
Figure 14:
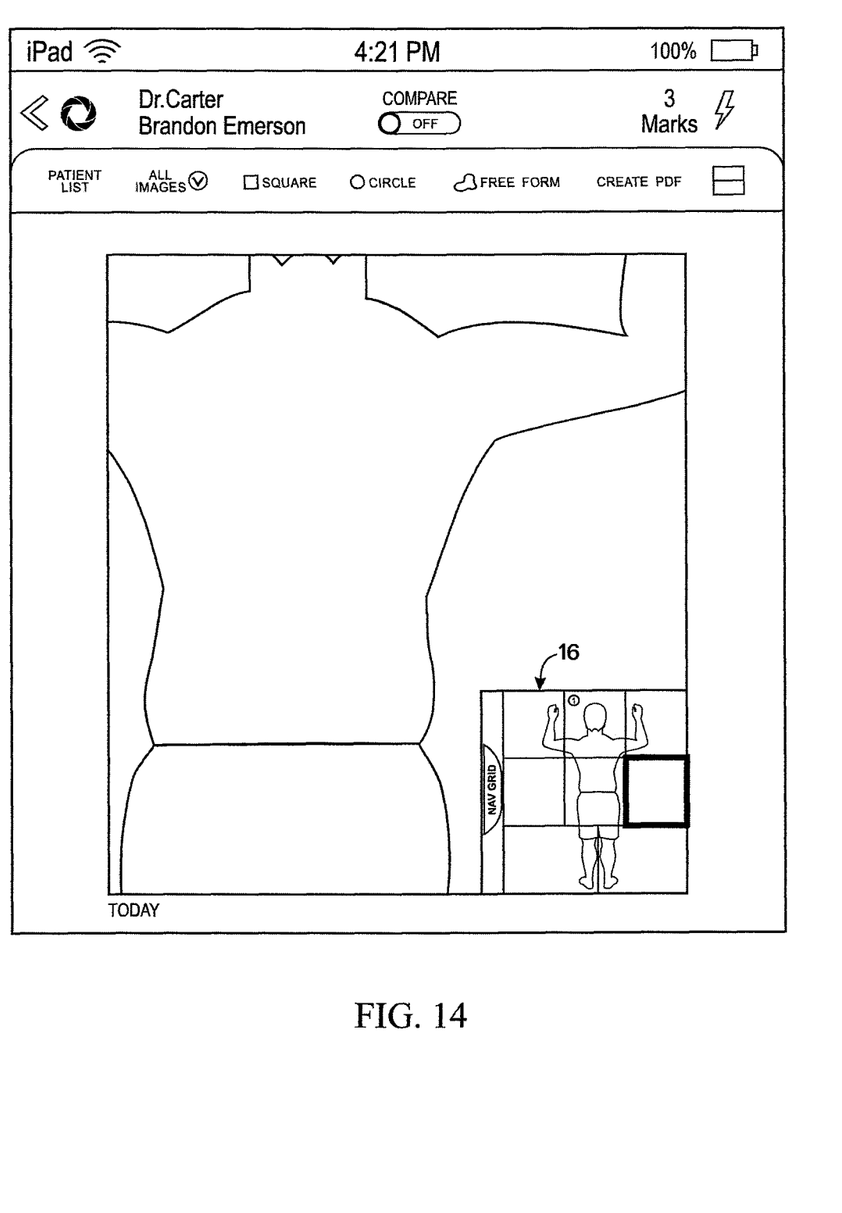
FIG. 14 is a GUI screen shot showing a reduced size image of a total body navigational grid of a user/patient that corresponds to eight high resolution camera images with the middle right tile/section of the navigational grid shown selected and the associated high resolution camera image shown magnified for more in depth viewing.

FIG. 5 is a front perspective view of the front panel 406 of the imaging apparatus 400 having openings contained therein for the camera lenses and the light panels. A plurality of circular openings 428 are positioned within and through the front panel 406 such that they coincide directly with each of the plurality of high resolution cameras 518, respectively, that are secured to the frame 420 so that the lenses of the high resolution cameras 518 can be seen from the enclosed interior area 402 of the imaging apparatus. Similarly, a single opening 429 is positioned within and through the front panel 406 such that it coincides directly with the wide angle lens camera 516 that is secured to the frame 420 so that the lens of wide angle lens camera 516 can be seen from the enclosed interior area 402 of the imaging apparatus. At least two vertically oriented rectangular openings 430 are positioned on opposing sides of the cameras 516, 518 so that a light panel 422 can be inserted into each vertically oriented rectangular opening 430. The light panels 422 can be seen from the enclosed interior area 402 of the imaging apparatus 400 and function to provide adequate lighting for the cameras 516, 518 in order for the cameras 516, 518 to produce readable images. The image produced from wide angle lens camera 516 is a total body image of the user while the images produced with the high resolution cameras 518 are high resolution body part images of the user. FIG. 6 shows an interior view of the front panel 406 and other interior imaging apparatus components as seen from the enclosed interior area 402 of the imaging apparatus 400.

In practice, a user/patient is positioned within the imaging apparatus for a specific pose. Images are then captured using the plurality of cameras. As previously described above in reference to FIGS. 4-6, in one exemplary embodiment, there are eight high resolution cameras in a 3×3×2 configuration which are used to capture body part images. There is also a camera with a wide angle lens that is mounted between the two rows of three high resolution cameras as shown. The camera with the wide angle lens is used to capture a full body image. Capture of all of the images is triggered by software so that all nine images are taken simultaneously including the eight body part images and the one full body image. The process of taking nine simultaneous images with the nine cameras is repeated seven times for a total of seven different poses that the user/patient is instructed to take for imaging.

All of the images are then post processed, preferably into a tiled TIFF or JPEG format for the viewing application. The viewing application arranges the eight high resolution body part images for a particular pose and associates them with the lower resolution full body image which is used for navigation. During use, a health care professional (such as a physician or health care assistant) views the seven full body images (which represent the seven different poses taken by the user/patient) on the viewing application. The health care professional then selects one full body image for review. Once the full body image is selected, the health care professional can click on or select a specific section or tile of the full body image. The high resolution body part image (taken with one of the eight high resolution cameras) associated with that specific body section or tile of the total body image taken by the wide angle lens camera then appears for close up review, zooming, and annotation. As can be seen in FIGS. 7-14, once a section or tile of the full body image navigational grid is selected, the high resolution body part image associated with that section or tile of the full body image typically includes many more parts of the user's body image than that shown in the section or tile of the full body image navigational grid. This is because the high resolution body part image is produced from one of the eight high resolution cameras and the images taken by any one of those eight high resolution cameras will overlap. However, the system and apparatus of the present invention does not have to process the overlapping images in a way that involves tying the overlapping images together. Therefore, the system and apparatus of the present invention provide for an easy, accurate, reliable and efficient means for obtaining and viewing the total body image, and particularly total body high resolution skin images, of a user or patient. Further review, zooming, and annotation of the high resolution body part images may be carried out, for example, like the process described in patent application having Ser. No. 14/860,509.

FIGS. 7-14 show exemplary screen shots of a graphical user interface seen by a physician or health care assistant (i.e. a health care professional) while viewing skin images (or body images) of a user/patient. The total body image taken with the camera having a wide angle lens is shown in the lower right hand corner of the screen shot and is used as a navigational grid. The health care professional selects the specific segment or tile of the full body image that they want to view and the high resolution body part image associated with that specific body section or tile appears on the large portion of the screen. This larger specific image can then be reviewed, made larger, and annotations can be made concerning what is seen in the image.

As previously stated, one example of a process for reviewing, expanding, and annotating with regard to a specific high resolution image is described in patent application having Ser. No. 14/860,509, and is herein incorporated by reference to be used with the system and apparatus described in this present invention. Further, as previously described in Ser. No. 14/860,509, an area of concern can be compared with previous recorded images of the same area of concern so that a physician or health care worker has a side by side comparison of the area of concern taken at different times. Additional screen shots may also be used for recording a diagnosis and/or medical code that relate to the imaged area of concern and/or recording any notes that relate to the imaged area of concern. Finally, all of the recorded and archived images and data can be shared wirelessly or via wired connection with the patient, other health care professionals, and/or health care related entities.

The invention claimed is:

1. A total body imaging apparatus comprising:
   an enclosed interior area;
   a camera with a wide angle lens positioned to capture a total body image of a user located in the enclosed interior area; and
   eight high resolution cameras positioned to capture different body portions of the user that together form a total body image of the user, said eight high resolution cameras being located within the enclosed interior area; and
   a computer processing unit in communication with at least one program application that triggers the wide angle lens camera and the eight high resolution cameras to simultaneously capture images and to arrange eight high resolution body part images taken with the eight high resolution cameras for a particular pose and associate them with the total body image captured with the wide angle lens camera for the same pose.

2. The total body imaging station of claim 1 wherein the enclosed interior area comprises a front panel which includes a plurality of openings therein positioned in front of the wide angle lens camera and the eight high resolution cameras such that a lens of each of said wide angle lens camera and said eight high resolution cameras can be seen through each of said respective plurality of openings.

3. The total body imaging apparatus of claim 1 wherein the wide angle lens camera is positioned between two rows of cameras that comprise the eight high resolution cameras.

4. The total body imaging apparatus of claim 1 wherein the eight high resolution cameras are configured to form a first row of three cameras, a second row of three cameras located below the first row of three cameras, and a third row of two cameras located below the second row of three cameras.

5. The total body imaging apparatus of claim 4 wherein the wide angle lens camera is positioned between the first row of three high resolution cameras and the second row of three high resolution cameras.

6. The total body imaging, apparatus of claim 5 wherein the enclosed interior area comprises a front panel which includes a plurality of openings therein positioned in front of the wide angle lens camera and the eight high resolution cameras such that a lens of each of said wide angle lens camera and said eight high resolution cameras can be seen through each of said respective plurality of openings.

7. The total body imaging apparatus of claim 5 wherein the program application uses the total body image as a navigational grid by sectioning the total body image into tiles that correspond to the location of the eight high resolution cameras and their related high resolution body part images where any of the eight tiles can be selected to magnify and further view in more detail an area of skin within a high resolution body part image that is associated with the selected tile.

8. The total body imaging apparatus of claim 7 wherein the program application further includes a reduced size image of the eight tile navigational grid displayed on a high resolution body part image associated with a selected tile of the navigational grid.

9. The total body imaging apparatus of claim 8 wherein the reduced size image of the eight tile navigational grid is displayed on a lower right side of the high resolution body part image associated with the selected tile of the navigational grid.

10. The total body imaging apparatus of claim 8 wherein the program application includes the ability to further magnify and annotate the high resolution body part image associated with the selected tile of the eight tile navigational grid.

11. A total body imaging system comprising:
    a camera with a wide angle lens positioned to capture a total body image of a user;
    a plurality of high resolution cameras positioned to capture different body portions of the user's total body where the wide angle lens camera and the plurality of high resolution cameras capture images simultaneously; and
    a computer processing unit in communication with at least one program application that arranges high resolution body part images taken with the plurality of high resolution cameras for a particular pose and associates them with the total body image of the user captured with the wide angle lens camera.

12. The total body imaging system of claim 11 wherein the at least one program application uses the total body image as a navigational grid by sectioning the total body image into sections that correspond to the location of the plurality of high resolution cameras and their related high resolution body part images where any of the sections can be selected to magnify and further view in more detail an area of skin within a high resolution body part image that is associated with a selected section.

13. The total body imaging system of claim 12 wherein the at least one program application further includes a reduced size image of the tiled navigational grid displayed on a high resolution body part image associated with a selected section of the navigational grid.

14. The total body imaging system of claim 13 wherein the reduced size image of the sectioned navigational grid is displayed on a lower right side of the high resolution body part image associated with the selected section of the navigational grid.

15. The total body imaging system of claim 14 wherein the at least one program application includes the ability to further magnify and annotate the high resolution body part image associated with the selected section of the sectioned navigational grid.

* * * * *